United States Patent [19]

Lee et al.

[11] Patent Number: 5,571,822
[45] Date of Patent: Nov. 5, 1996

[54] ANTITUMOR COMPOUNDS

[75] Inventors: Kuo-Hsiung Lee, Chapel Hill, N.C.; Sheng-Chu Kuo, Tai-Chung; Tian-Shung Wu, Tainan City, both of Taiwan; Hui K. Wang, Carboro; Leping Li, Chapel Hill, both of N.C.

[73] Assignee: The University of North Carolina at Chapel Hill, Chapel Hill, N.C.

[21] Appl. No.: 316,409

[22] Filed: Sep. 30, 1994

Related U.S. Application Data

[63] Continuation-in-part of PCT/US93/06893, Jul. 22, 1993.
[51] Int. Cl.$^6$ .................... C07D 215/38; C07D 215/233
[52] U.S. Cl. ................................. 514/312; 546/154
[58] Field of Search ........................... 546/154; 514/312

[56]         References Cited

U.S. PATENT DOCUMENTS

| | | | |
|---|---|---|---|
| 3,725,413 | 4/1973 | Genzer et al. | 546/90 |
| 5,126,351 | 6/1992 | Luzzio et al. | 514/291 |

FOREIGN PATENT DOCUMENTS

| | | |
|---|---|---|
| 0343574 | 11/1989 | European Pat. Off. |
| 0341104 | 11/1989 | European Pat. Off. |
| 2276049 | 6/1975 | France |
| 56-007784 | 1/1981 | Japan |
| 94/02145 | 2/1994 | WIPO |

OTHER PUBLICATIONS

Chen, B-C., et al., "A Versatile Synthesis of 2–Alkyl and 2–Aryl 4–Quinolones," *Synthesis* 5: 482–483 (1987).

Cheng, C. C., "A Common Structural Pattern Among Many Biologically Active Compounds of Natural and Synthetic Origin," *Medical Hypothesis* 20: 157–172 (1986).

Jiang, J. B., et al., "Synthesis and Biological Evaluation of 2–Styrylquinazolin–4(3H)–ones, a New Class of Antimitotic Anticancer Agents Which Inhibit Tubulin Polymerization," *J. Med. Chem.* 33: 1721–1728 (1990).

Kalinin, V. N., et al., "A New Route To 2–Aryl–4–Quinolones Via Palladium–Catalyzed Carbonylative Coupling of o–Iodoanilines With Terminal Arylacetylenes," *Tetrahedron Letters* 33(3): 373–376 (1992).

Kasahara, A., et al., "A new synthesis of 2–aryl–4–quinolones," *Chemistry and Industry* 4: 121 (1981).

Kuo, S–C., et al., "Synthesis and Cytotoxicity of 1,6,7, 8–Substituted 2–(4'–Substituted phenyl)–4–quinolones and Related Compounds: Identification as Antimitotic Agents Interacting with Tubulin," *J. Med. Chem.* 36: 1146–1156 (1993).

Venturella, P., and A. Bellino, "On the Reactions Between Ethyl Benzoylacetate and Anisidines," *J. Heterocyclic Chem.* 12(4): 669–673 (1975).

Venturella, P., et al, "Synthesis of 1–methyl–2–phenyl–5–hydroxy–4–quinolone and improved synthesis of edulein," *Gazzetta Chimica Italiana* 100(7): 678–681 (1970).

*Primary Examiner*—C. Warren Ivy
*Assistant Examiner*—D. Margaret M. Mach
*Attorney, Agent, or Firm*—Vincent M. Powers; Susan T. Evans

[57]         ABSTRACT

A method of inhibiting tumor-cell growth in a mammalian subject, by administering a therapeutically effective amount of a selected 2-phenyl-4-quinolone compound. The selected compound shows unexpectely high activity against a variety of solid tumor cells.

20 Claims, 1 Drawing Sheet

ANTITUMOR COMPOUNDS

This application is a continuation-in-part of PCT Application No. PCT/US93/06893 filed Jul. 22, 1993.

Field of the Invention

The present invention relates to certain 2-aryl-4-quinolone compounds and their use as anti-tumor agents.

REFERENCES

Bandurco, V. T., et al., *J. Med. Chem.* 30:1421 (1987).

Boyd, M. R., Status of the NCI preclinical antitumor drug discovery screen. In *Cancer: Principles and Practice of Oncology Updates* (DeVita, V. T., et al., eds.), pp. 1–12 (1989).

Chen, B. C., et al., *Synthesis*, 487 (1987).

Chong, R. J., et al., *Tetrahedron Lett.*, 27:5323–5326 (1986).

Desai, K., et al., *Indian J. Chem.* 5:170 (1967).

Getahun, Z., et al., *J. Med. Chem.*, 35:1058–1067 (1992).

Grever, M. R., et al., *Seminars Oncol.* 19:622 (1992).

Hamel, E., et al., *Biochemistry*, 2:4173–4184 (1984).

Kuo, S. C., et al., *J. Med. Chem.* 36:1146 (1993). Lee, K. H., et al., *J. Nat. Prod.*, 44:530–535 (1981).

Li, L., et al., *J. Med. Chem.* 37:1126 (1994).

Lin, C. M., et al., *Biochemistry* 28:6984 (1989).

Monks, A., et al., *J. Natl. Cancer Inst.*, 83:757–766 (1991).

Simpson, J. C. E., et al., *J. Chem. Soc.*, 646 (1945).

BACKGROUND

Quinolones have been widely studied as antibacterial agents. The antibacterial activity of quinolones appears to be related, at least in part, to the ability of the compounds to bind to and inhibit DNA gyrase.

More recently, additional therapeutic uses for quinolone compounds have been reported. For example, EP Publication 341104 A3 (1989) discloses a class of substituted quinolone compounds for anticancer use. EP 343574 A1 describes 2-aryl-4-quinolones said to be useful for increasing heart muscle contractility without increasing heart rate.

Although, certain 2-phenyl-4-quinolone compounds have been disclosed for anticancer use, there is a need to identify compounds having particularly high anticancer activity, for minimizing drug dosages and hence, the toxicity effects that may accompany such compounds.

SUMMARY OF THE INVENTION

In accordance with one aspect, the invention includes a method of inhibiting tumor cell growth in a mammalian subject, comprising administering to the subject a therapeutically effective amount of a 2-phenyl-4-quinolone compound represented by the formula:

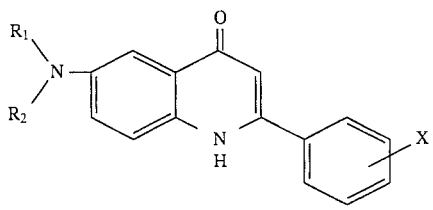

wherein X is a selected from the group consisting of H, F, Cl, Br, I, $CH_3$, $CF_3$, OH, $OCH_3$, $OCF_3$, $OCH_2CH_3$, $NH_2$, $NHCH_3$, $N(CH_3)_2$, O-benzyl, —C(=O)—$R_0$, —C(=O)—$OR_0$, where $R_0$ is a lower alkyl group; where and $R_1$ and $R_2$ (i) are lower alkyl groups or (ii) taken together, form a chain having the form —$(CH_2)_m Y (CH_2)_n$—, where Y is $CH_2$, O, or S; m and n are each greater than 1; and the sum of m and n is between 3 and 6.

Substituent X can occupy an ortho, meta, or para position on the 2-phenyl ring. Preferably, X is a meta substituent. In a particular embodiment, X is meta-$OCH_3$ or meta-$OCF_3$.

In another preferred embodiment, $NR_1R_2$ is selected from the group consisting of $N(CH_3)_2$, N-pyrrolidinyl, N-piperidyl, and N-morpholinyl. In a particularly preferred embodiment, $NR_1R_2$ is N-pyrrolidinyl.

The compounds show unexpectedly high antitumor activity against a variety of tumor cell lines, including cell lines derived from solid tumors, such as leukemia, non-small cell lung, colon, central nervous system, melanoma, ovary, renal, prostate, and breast cancers.

Accordingly, in a related aspect, the invention includes a method of treating a tumor in a mammalian subject, by administering to the subject a 2-phenyl-4-quinolone compound of the type above, in an amount effective to reduce tumor growth in the subject.

In another aspect of the invention, the 2-aryl-4-quinolone compounds of the invention are effective to overcome multiple drug resistance in tumor cells, effectively inhibiting tumor cells which are drug-resistant to doxorubicin, vincristine, and/or VP-16 (an etoposide anti-tumor agent). In this aspect, the invention includes, in a treatment regimen for inhibiting growth of a tumor in a subject, in which the tumor has become progressively more refractory to inhibition of growth by doxorubicin, vincristin, or VP-16, a method for inhibiting the growth of the tumor, by administering to the subject, a 2-aryl-4-quinolone compound, in an amount effective to inhibit tumor growth in the treated subject.

The invention also includes a pharmaceutical composition which contains a 2-aryl-4-quinolone compound of the type described above, for use in inhibiting the growth of tumor cells.

These and other objects and features of the invention will become more fully apparent when the following detailed description of the invention is read in conjunction with the accompanying drawings.

DETAILED DESCRIPTION OF THE INVENTION

I. Definitions

Figure 1:
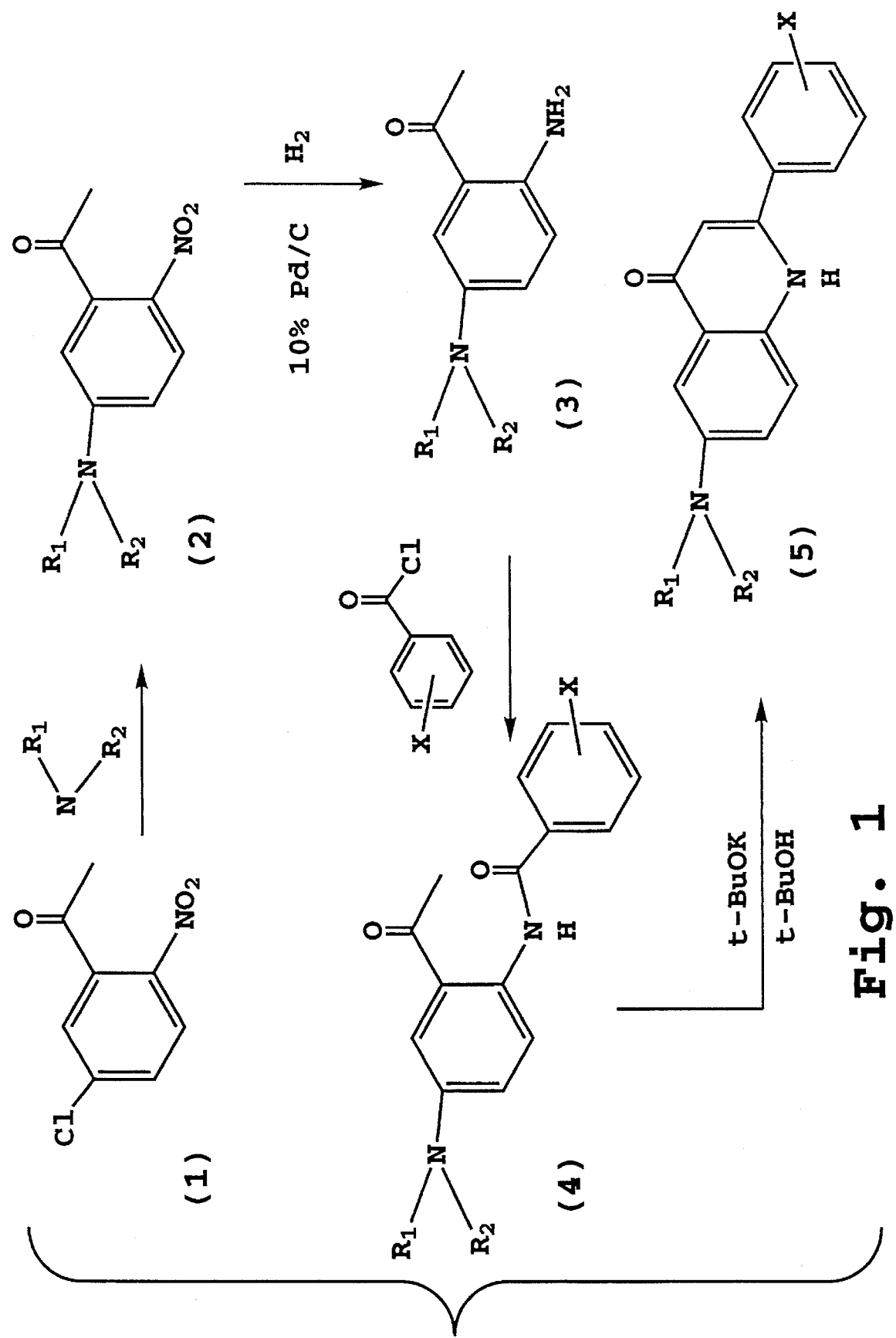
FIG. 1 shows a synthesis scheme for preparing highly active 2-aryl-4-quinolone compounds in accordance with the invention.

As used herein, the terms below have the following meanings.

By "administering a therapeutically effective amount of a 2-phenyl-4-quinolone compound" is meant that a amount of such compound in a pharmaceutically acceptable form, which may be a pharmaceutically acceptable salt thereof, is administered in an amount effective to achieve a compound concentration at the tumor site or in the bloodstream effective to inhibit growth of target tumor cells in the subject.

"Lower alkyl" refers to an alkyl radical of one to four carbon atoms, as exemplified by methyl, ethyl, n-butyl, i-butyl, t-butyl, including fluorinated, monohydroxy, or chlorinated forms thereof.

For quinolone compounds described below, the following numbering scheme is employed:

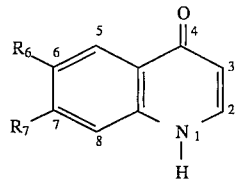

II. 2-Aryl-4-Quinolone Compounds

This section describes methods for synthesizing certain 6-amino-substituted 2-phenyl-4-quinolone compounds which have unexpectedly high antitumor activity against a variety of tumor cell lines, and which are therapeutically useful for antitumor treatment.

2-Phenyl-4-quinolone compounds can be prepared using synthetic routes available in the published scientific and patent literature (e.g., Desai et al., 1967; Fuson et al., 1946; Chen et al., 1987; Chong et al., 1982; and Li et al., 1994).

One general synthetic scheme for preparing 6-dialkylamino-substituted 2-phenyl-4-quinolones, is illustrated in FIG. 1. In the first step, 2-nitro-5-chloacetophenone is reacted with an appropriate amine of formula $NHR_1R_2$ defined above, followed by hydrogenation over 10% Pd/C to convert the 2-nitro group to an amino group, yields the desired 5-amino-substituted 2-aminoacetophenone. Reaction of this product with an appropriately substituted benzoyl chloride affords biaryl amide 4, and subsequent treatment with potassium tert-butoxide/t-butanol yields desired 6-substituted-quinolone 5.

Related quinolone analogs can be prepared based on variations of the above procedure. For example, 6,7-methylenedioxy quinolones, such as compounds 10–19 in Table I, can be prepared by suitable modification of the FIG. 1 scheme, using 1,2-methylenedioxyacetophenone as starting material (e.g., Example 1A).

6-Acetylamido-2-phenyl-4-quinolone can be prepared as follows. Nitration of 3-acetamidoacetophenone followed by hydrogenation affords 2-amino-5-acetamidoacetophenone. The desired 2-phenyl-4-quinolone is then formed by reaction with an appropriately substituted benzoyl chloride followed by appropriate steps from FIG. 1 (e.g., Example 1P).

A slightly different procedure can be used to make a 6-benzamido-derivative. Here, the 2-nitro-5-acetamidoacetophenone formed by nitration of 3-acetamidoacetophenone is hydrolyzed in KOH/ethanol to give 2-nitro-5-aminoacetophenone. The latter product is reacted with benzoylchloride, forming 2-nitro-5-benzoylamidoacetophenone. Hydrogenation (10% Pd/C) of the product affords 2-amino-5-benzoylamidoacetophenone which can be used in the FIG. 1 scheme to produce the desired 6-benzoylamido-2-phenyl-4-quinoline (Ex. 1X).

Quinolone compounds containing a free amino group at the 6-position (e.g., compounds 20–22 in Table I) can be prepared using orthoacetylaminoacetophenone as starting material. Treatment of this compound under nitration conditions affords 2-acetamido-5-nitroacetophenone. results in formation of 2-amino-5-nitroacetophenone. After reaction of this compound with a benzoylchloride derivative as in FIG. 1, reduction of the 5-nitro group by Pd/C hydrogenation, followed by potassium tert-butoxide-mediated ring-closure (as in FIG. 1), yields the desired 6-amino-2-phenyl-4-quinolone compound (e.g., Examples 1K–1M).

2-Phenylquinolones can be purified by silica gel chromatography or by recrystallization from dimethylformamide or a $CHCl_3$/methanol mixture. Chemical characterization of particular compounds prepared as above methods are detailed in the Example section below.

III. Treatment Method

The invention includes a method of treating a tumor in a mammalian subject, by administering to the subject a 2-aryl-4-quinolone compound in an amount effective to inhibit growth of the tumor cells in the subject.

A. Tumor-Cell Toxicity

Selected 2-phenyl-4-quinolones were assayed using an in vitro, disease-oriented antitumor screen run by the National Cancer Institute (NCI) (e.g., Boyd 1989). The screen involved approximately 60 different cell lines and is a useful indicator of in vivo antitumor activity for a broad variety of tumor types (Grever et al., 1992; Monks et al., 1991). The cell lines tested included cells derived from the following solid tumor types: leukemia, non-small cell lung, colon, the central nervous system (CNS), melanoma, ovarian, renal, prostate, and breast cancers.

Table I gives selected chemical information regarding the compounds tested, with cytotoxicity results for 12 representative cell lines shown in Table II. With reference to Table I, the compounds included 6,7-methylenedioxy compounds (compounds 10–19 and 34–36), 6-amido compounds (compounds 25–27 and 33), and several 6-amino compounds (compounds 20–23 and 28–32).

The antitumor activities shown in Table II are expressed in terms of log $GI_{50}$, where $GI_{50}$ was the molar concentration of compound effective to reduce cell growth by 50%.

As can be seen from Table 2, all compounds tested showed cytotoxic activities ≦−4 for all cell lines shown. For the 6,7-methylenedioxy compounds tested for cytotoxicity (compounds 10–19), individual log values ranged between about −4 and −7.8, with

TABLE I

| compd | $R_6$ | $R_7$ | $R_{3'}$ | ITP[a] $IC_{50}(\mu M) \pm SD$ | ICB[b] (% inhibition) | formula[c] | mp, °C. | yield, % |
|---|---|---|---|---|---|---|---|---|
| 10 | OCH$_2$O | | NH$_2$ | 0.73 ± 0.2 | 16 ± 7 | C$_{16}$H$_{12}$N$_2$O$_3$.0.5H$_2$O | >250[d] | 43 |
| 11 | OCH$_2$O | | NHCH$_3$ | 0.65 ± 0.1 | 17 ± 11 | C$_{17}$H$_{14}$N$_2$O$_3$.0.2H$_2$O | 273–274[d] | 30 |
| 12 | OCH$_2$O | | OH | 0.47 ± 0.1 | 26 ± 3 | C$_{16}$H$_{11}$NO$_4$.H$_2$O | >300[d] | 27 |
| 13 | OCH$_2$O | | F | 0.53 ± 0.1 | 51 ± 3 | C$_{16}$H$_{10}$FNO$_3$.0.5H$_2$O | >300[d] | 68 |
| 14 | OCH$_2$O | | Cl | 0.37 ± 0.03 | 45 ± 7 | C$_{16}$H$_{10}$ClNO$_3$ | 190—190 | 70 |
| 15 | OCH$_2$O | | Br | 0.53 ± 0.1 | 26 ± 3 | C$_{16}$H$_{10}$BrNO$_3$ | >300 | 69 |
| 16 | OCH$_2$O | | CF$_3$ | 0.82 ± 0.2 | 5 ± 7 | C$_{17}$H$_{10}$F$_3$NO$_3$ | 281–184[d] | 72 |
| 17 | OCH$_2$O | | OCF$_3$ | 0.50 ± 0.1 | 40 ± 5 | C$_{17}$H$_{10}$F$_3$NO$_4$ | >300 | 80 |
| 18 | OCH$_2$O | | OCH$_2$CH$_3$ | 0.47 ± 0.1 | 40 ± 2 | C$_{18}$H$_{15}$NO$_4$ | >280[d] | 56 |
| 19 | OCH$_2$O | | OBz | 0.45 ± 0.03 | 26 ± 5 | C$_{23}$H$_{17}$NO$_4$.0.75H$_2$O | >300[d] | 60 |
| 20 | NH$_2$ | H | Cl | 6.1 ± 1 | | C$_{15}$H$_{11}$ClN$_2$O | 261—263[d] | 60 |
| 21 | NH$_2$ | H | CF$_3$ | >40.0 | | C$_{16}$H$_{11}$F$_3$N$_2$O | >280[d] | 68 |
| 22 | NH$_2$ | H | OCH$_3$ | 8.7 ± 3 | | C$_{16}$H$_{14}$N$_2$O$_2$.1.5H$_2$O | 124–126 | 64 |
| 23 | N(CH$_3$)$_2$ | H | OCH$_3$ | 0.38 ± 0.1 | 14 ± 8 | C$_{18}$H$_{18}$N$_2$O$_2$.0.2H$_2$O | 246–248[d] | 61 |
| 24 | Cl | H | OCH$_3$ | 0.70 ± 0.2 | 16 ± 5 | C$_{16}$H$_{12}$ClNO$_2$ | 283–285 | 65 |
| 25 | NHCOCH$_3$ | H | F | 1.5 ± 0.5 | | C$_{17}$H$_{13}$FN$_2$O$_2$ | >300 | 62 |
| 26 | NHCOCH$_3$ | H | Cl | 2.3 ± 0.7 | | C$_{17}$H$_{13}$ClN$_2$O$_2$.0.5H$_2$O | >300 | 64 |
| 27 | NHCOCH$_3$ | H | OCH$_3$ | 2.1 ± 0.5 | | C$_{18}$H$_{16}$N$_2$O$_3$ | 298–300 | 60 |
| 28 | pyrrolidinyl | H | OCH$_3$ | 0.44 ± 0.02 | 84 ± 6 | C$_{20}$H$_{20}$N$_2$O$_2$ | 276–278[d] | 68 |
| 29 | pyrrolidinyl | H | OCF$_3$ | 0.72 ± 0.2 | 58 ± 5 | C$_{20}$H$_{17}$F$_3$N$_2$O$_2$ | 280–282[d] | 66 |
| 30 | piperidinyl | H | OCH$_3$ | 0.78 ± 0.2 | 53 ± 6 | C$_{21}$H$_{22}$N$_2$O$_2$.0.3H$_2$O | 274–276[d] | 70 |
| 31 | morpholinyl | H | OCH$_3$ | 0.36 ± 0.1 | 43 ± 10 | C$_{20}$H$_{20}$N$_2$O$_3$.0.5H$_2$O | 280–282[d] | 73 |
| 32 | 4-methylpiperazinyl | H | OCH$_3$ | 14 ± 2 | | C$_{21}$H$_{23}$N$_3$O$_2$ | 273–275[d] | 69 |
| 33 | PhCONH | H | OCH$_3$ | 1.3 ± 0.07 | | C$_{23}$H$_{18}$N$_2$O$_3$ | >300 | 43 |
| 34 | OCH$_2$O | | H | 0.63 ± 0.2 | 26 ± 10 | | | |
| 35 | OCH$_2$O | | OCH$_3$ | 0.57 ± 0.1 | 39 ± 8 | | | |
| 36 | OCH$_2$O | | N(CH$_3$)$_2$ | 0.70 ± 0.03 | 29 ± 7 | | | |
| colchicine | | | | 0.80 ± 0.07 | | | | |
| podophyllotoxin | | | | 0.46 ± 0.02 | 84 ± 2 | | | |
| combretastatin A-4 | | | | 0.53 ± 0.05 | 94 ± 2 | | | |
| dihydrocombretastatin A-4 | | | | 0.63 ± 0.03 | 65 ± 4 | | | |

[a] ITP = inhibition of tubulin polymerization.
[b] ICB = inhibition of colchicine binding and evaluated only when polymerization IC$_{50}$ ≦ 1.0 μM.
[c] All compounds were analyzed for C, H. and N, and results agreed to ±0.4% of the theoretical values.
[d] Decomposed.

TABLE II cytotoxocity logGI$_{50}$ (M)$^c$

| comps | average logGI$_{50}$$^d$ | K-562 | NCI-H226 | HCT116 | KM202L | SF-268 | SF-295 | SK-Mel-5 | OVCAR-3 | OVCAR-4 | RXF-393 | DU-145 | MDA-N |
|---|---|---|---|---|---|---|---|---|---|---|---|---|---|
| 10 | -5.79 | -6.05 | -5.66 | -6.32 | -6.15 | -6.12 | -5.62 | -6.03 | nt$^e$ | -4.41 | -6.22 | nt | nt |
| 11 | -6.29 | -6.40 | -6.27 | -6.61 | -6.48 | -5.26 | -6.49 | -6.35 | -6.47 | nt | -6.44 | nt | nt |
| 12 | -5.51 | -6.14 | nt | -5.74 | -5.48 | -5.64 | -5.26 | -5.83 | nt | nt | nt | nt | nt |
| 13 | -6.47 | -6.47 | -6.02 | -6.66 | nt | -6.18 | -6.85 | -6.57 | -6.54 | nt | -6.79 | nt | nt |
| 14 | -6.30 | -6.51 | -5.74 | -6.47 | -6.57 | -6.21 | -6.65 | -6.68 | -6.74 | >-4.12 | -5.62 | nt | nt |
| 15 | -5.48 | -5.46 | -5.42 | -5.47 | -5.51 | -5.52 | -6.48 | -5.36 | -5.37 | —$^f$ | -5.79 | nt | nt |
| 16 | -5.56 | nt | -5.24 | -5.70 | -5.86 | -5.34 | -6.00 | -5.89 | -5.93 | -5.00 | -5.79 | -5.53 | -6.09 |
| 17 | -6.38 | -7.44 | -6.71 | -7.85 | -7.44 | nt | -7.59 | -6.77 | -7.20 | -7.59 | -7.39 | -7.34 | <-8.0 |
| 18 | -6.65 | -7.35 | -6.49 | -6.76 | -6.74 | -6.57 | -7.19 | -6.72 | -6.78 | nt | -6.56 | -6.60 | -7.75 |
| 19 | -6.17 | -6.44 | -6.64 | -6.41 | -6.65 | -4.89 | -6.35 | -6.55 | -6.61 | — | -6.39 | -5.96 | -6.84 |
| 20 | -5.26 | -5.66 | -5.27 | nt | -5.50 | -5.17 | -5.56 | nt | -5.54 | — | -5.74 | nt | nt |
| 21 | -4.40 | -4.45 | -4.41 | 4.28 | -4.46 | -4.23 | -4.55 | nt | -4.58 | -4.20 | -4.63 | -4.36 | -4.98 |
| 22 | -5.34 | -5.68 | -5.23 | -5.44 | -5.46 | -5.25 | -5.51 | nt | -5.56 | -4.08 | -5.72 | -5.41 | -6.12 |
| 23 | -7.52 | -8.05 | -7.35 | nt | -8.34 | -7.36 | -7.81 | -7.59 | -7.82 | -5.26 | -7.73 | -7.46 | -8.77 |
| 24$^g$ | | | | | | | | | | | | | |
| 25 | -4.82 | -5.21 | -4.63 | -5.34 | -4.45 | -4.59 | -4.41 | -5.44 | -5.99 | — | — | — | -5.78 |
| 26 | -4.98 | -5.38 | -4.89 | -5.36 | -4.73 | -5.33 | -4.73 | nt | -5.47 | — | -5.09 | -4.56 | -5.71 |
| 27 | -4.70 | -5.34 | -4.27 | -4.95 | -4.49 | -5.26 | -4.35 | nt | -5.66 | -4.71 | -5.28 | -4.95 | -5.49 |
| 28 | -8.73 | <-9.00 | <-9.00 | <-9.00 | <-9.00 | <-9.00 | <-9.00 | <-9.00 | <-9.00 | -5.70 | <-9.00 | <-9.00 | <-9.00 |
| 29$^g$ | | | | | | | | | | | | | |
| 30$^g$ | | | | | | | | | | | | | |
| 31 | -7.25 | -7.61 | -7.47 | -7.57 | -7.47 | -7.27 | -7.31 | -7.45 | -7.70 | -5.20 | -7.91 | -7.36 | -8.08 |
| 32 | -5.81 | -6.27 | -5.82 | -6.36 | -5.82 | -5.73 | -5.74 | -6.04 | -6.11 | >-5.0 | -6.34 | -5.60 | -6.70 |
| 33$^g$ | | | | | | | | | | | | | |

$^a$Data obtained from NCI's in vitro disease-oriented human tumor cells screen (see Grever et al. (1992) and Monks et al. (1991) for detail). $^b$K-562, leukemia cell line; NCI-H226, non-small cell lung cancer cell line; HCT-116 and KM20L2, colon cancer cell lines; OVCAR-3 and OVCAR-4, ovarian cancer cell lines; RXF-393, renal cancer cell line; SK-Mel-5, melonoma; SF-268 and SF-295, CNS tumor cell lines; DU-145, prostate cancer cell line; MDA-N, breast cancer cell line. $^c$Log concentrations which reduced cell growth to 50% of level at start of experiment. $^d$average logGI$_{50}$ values calculated from all cell lines tested. $^e$"nt" means not tested. $^f$"—" means logGI$_{50}$ is greater than -4. $^g$Cytotoxicity assay is pending.

average values of between −5.5 (compounds 12 and 15) and −6.65 (compound 18).

6-Amino compounds 20–22 were generally less active, showing average log values of −4.4 to −5.0. 6-Acetamido compounds 25–27 showed comparably moderate activity (Table II).

Surprisingly, 6-N,N-dialkylamino compounds demonstrated by far the most potent activities. Compound 23, which contains a 6-dimethylamino group, showed an average activity value of −7.5, at least 0.9 log units lower than the average activities found for compounds 10–22, 25–27, and 32. With regard to individual cell lines, the activities found for compound 23 were in every case lower than those observed for compounds 10–22, 25–27, and 32.

Substitution of the dialkylamino moiety with a larger pyrrolidinyl moiety, as in compound 28, resulted in the most potent activity of all, with an average activity $\leq -8.73$. Further, as can be seen from the table, the potency of compound 28 exceeded the sensitivity of the testing protocol for many of the cell lines tested.

Compound 31, which contains a 6-morpholino group, also was shown to be highly potent, with an antitumor activity comparable to that of compound 23 above. However, substitution with an N-methylpiperazine moiety at the 6-position resulted in a significant decrease in activity, indicating that the presence of a readily protonatable amine (pK ~9) is deleterious to achieving high activity.

With reference to the compounds in Table 1 and activity data in Table 2, it can be seen that certain 6-N,N-dialkylamino moieties afford particularly high antitumor activity. A free amino group at the 6-position, on the other hand, affords significantly lower activity, indicating that the 6-N-alkyl groups are important. The electronic structure of the 6-position substituent is also important, as the presence of an acylamino moiety (compounds 25–27 and 33) affords only moderate antitumor activity. Thus, resonance delocalization of the 6-nitrogen atom inherent in an amide group leads to diminished activity.

With reference to structure 5 in FIG. 1, where $R_1$ and $R_2$ are as defined above, a cyclic amino substituent is preferred, as with the 5-membered ring structure (6-pyrrolidinyl group) in compound 28. Substitution with a larger ring structure, as with the morpholino group in compound 31, or with a pair of relatively small alkyl groups, as in compound 23, is less preferred.

With continued reference to structure 5 and Table II, it can be seen that antitumor activity is relatively insensitive to the size of substituents on the 2-phenyl ring. More generally, substitution at the meta position is preferred over the para position, which in turn is preferred over substitution at the ortho position.

The data in Table II demonstrate that the high-activity compounds of the invention, i.e., quinolone compounds having the structural features set forth in the Summary section above, are active against a broad range of human cancer types. A total of 9 different cancer cell types are represented in Table II (footnote b in Table II), all of which are significantly inhibited with nanomolar levels of the highly active compounds. Such high efficacies allow lower drug dosages to be administered, helping reduce deleterious systemic effects that may arise with higher dosages.

C. Interactions with Tubulin

Studies conducted in support of the present invention indicate that one mode of action of the 2-phenyl-4-quinolone compounds, as antitumor agents, is an ability to bind to tubulin and inhibit cell mitosis. To examine structure-function relationships between the 2-phenyl-4-quinolone compounds in Table I and inhibition of tubulin polymerization, the compounds were tested for inhibition of tubulin polymerization, and for inhibition of colchicine binding to tubulin, using methods detailed in Example 2. The results are given in Table 1, including comparison with the potent antimitotic compounds colchicine, podophyllotoxin, and combretastatin A-4. These three natural products all bind at the colchicine site of tubulin (Hamel, 1990; Lin, et al., 1990).

Most of the compounds tested were potent inhibitors of polymerization, with $IC_{50}$ values below 1.0 mM. The values were comparable to those for colchicine, podophyllotoxin, and combretastatin A-4 (Table I). Only compound 21 was inactive ($IC_{50}$>40 mM).

A variety of substituents at the 3'-position of the 4-phenyl ring were found to be well tolerated in 6,7-methylenedioxy compounds 10–19 (IC50<1.0 mM). These substituents include electron-donating groups such as $NH_2$, $NHCH_3$, OH, $OCF_3$, OEt, and OBz, and electron-withdrawing groups such as F, Cl, and Br. The sizes of the substituents ranged from small (H, compound 34) to large (OBz, compound 19) without significantly changing activity.

Compounds with a heterocyclic ring at the 6-position (28–31) were highly active (IC50<1.0 mM), except for compound 32 (IC50=14 mM), which contains a 1-methylpiperazinyl group at the 6-position. The non-cyclic 6-N,N-dimethylamino, compound 23, was also highly active (IC50=0.38 mM) in this assay.

As was observed with antitumor activity, the 6-$NH_2$ compounds (20 and 22) were moderately active, although compound 21 was inactive.

The most potent compounds ($IC_{50}$>14 μM) were also evaluated for inhibition of radiolabeled colchicine binding to tubulin (Table I under ICB heading). Selected compounds and radiolabeled colchicine were present in equimolar concentrations and in 5-fold molar excess over tubulin. As can be seen, the quinolone compounds with the highest antitumor activity were also strongest in inhibiting colchicine binding.

D. Treatment Methods

In the treatment method of the invention, a 2-aryl-4-quinolone compound of the type described in the Summary section is administered in a pharmaceutically effective amount, to reduce tumor growth in a mammalian subject.

During tumor treatment, the patient will typically receive periodic doses, e.g., biweekly doses of the drug, with the effectiveness of treatment being monitored by tumor biopsy, radiological methods, or blood enzyme levels, according to standard methods.

Administration of the compounds of the invention can be carried out via any of the accepted modes of administration of agents for similar utilities. Thus, administration can be, for example, oral, nasal, parenteral or topical. The formulations may take the form of solid, semi-solid, lyophilized powder, or liquid dosage forms, such as, for example, tablets, pills, capsules, powders, solutions, suspensions, emulsions, suppositories, retention enemas, creams, ointments, lotions, aerosols or the like, preferably in unit dosage forms suitable for simple administration of precise dosages.

The compositions typically include a conventional pharmaceutical carrier or excipient and may additionally include other medicinal agents, carriers, adjuvants, and the like. The antitumor compounds can be prepared in a pharmaceutically acceptable salt form according to standard methods, e.g., by acid/base titration or exchange with suitable counterions such as $K_+$, $Na_+$, $Mg_+$, or the like, for anionic antitumor compound, or with sulfate, chloride, or other suitable anions for potentially cationic antitumor compounds.

Preferably, the composition will be about 0.5% to 75% by weight of a compound or compounds of the invention, with the remainder consisting of suitable pharmaceutical excipients. For oral administration, such excipients include pharmaceutical grades of mannitol, lactose, starch, magnesium stearate, sodium saccharine, talcum, cellulose, glucose, gelatin, sucrose, magnesium carbonate, and the like. the composition may take the form of a solution, suspension, tablet, pill, capsule, powder, sustained-release formulation, and the like.

The active compounds of the formulas may be formulated into a suppository comprising, for example, about 0.5% to about 50% of a compound of the invention, disposed in a polyethylene glycol (PEG) carrier (e.g., PEG 1000 [96%] and PEG 4000 [4%]).

Liquid compositions can be prepared by dissolving or dispersing compound (about 0.5% to about 20%), and optional pharmaceutical adjuvants in a carrier, such as, for example, aqueous saline, aqueous dextrose, glycerol, ethanol and the like, to form a solution or suspension. The active compounds may be formulated into a retention enema.

If desired, the composition to be administered may also contain minor amounts of non-toxic auxiliary substances such as wetting or emulsifying agents, pH buffering agents, such as, for example, sodium acetate, sorbitan monolaurate, or triethanolamine oleate.

Methods for preparing such dosage forms are known or will be apparent to those skilled in the art; for example, see *Remington's Pharmaceutical Sciences* (1980). The composition to be administered will, in any event, contain a quantity of the prodrug and/or active compound(s) in a pharmaceutically effective amount for relief of the condition being treated when administered in accordance with the teachings of this invention.

An estimate of the appropriate therapeutic amount can be estimated based on $IG_{50}/EC_{50}$ values from in vitro cell growth inhibition studies, such as those described, using known tumor cell lines, and particularly cells related to the subject's tumor type or actually obtained from the subject.

The data in section B indicate that a local compound concentration between about 0.1 nM and about 100 nM, preferably between about 1 and 10 nM, can be effective to reduce tumor growth for a large variety of tumor-cell types. Doses effective to achieve these concentrations in the blood in human patients, either by parenteral, e.g., intravenous, or oral administration can be refined based on animal model studies, using known dose relationships between dose and pharmacokinetics between animal models and humans.

In a treatment regiment in which doxorubicin, a related anthracyline anti-tumor compound, VP-16 or a related etoposide compound, or vincristine or a related vinca alkaloid drug is used initially, and resistance to the anti-tumor compound is observed, the present invention also provides a method of inhibiting tumor cell growth in the subject. In this method, a 2-aryl-4-quinolone compound of the type above is administered in an amount effective to inhibit tumor growth.

Drug resistance in the initial phase of the regimen is evidenced by an increasingly larger drug dose needed to inhibit tumor growth. That is, the tumor becomes increasingly more refractory to growth inhibition by the drug. In the second phase of the regimen, in which a 2-aryl-4-quinolone compound is administered, either alone or in combination with the initial-phase drug, the effective drug dose of aryl quinolone is generally no higher than that required before drug resistance develops.

From the foregoing, it can be appreciated how the treatment method of the invention offers advantages in tumor treatment. The compound itself is readily synthesized, and can be administered either orally or parenterally, e.g., by intravenous administration. The mode of action of the compound, inhibiting tubulin formation necessary for cell mitosis, would tend to confine the effects of the compound to actively dividing cell. In this regard, studies carried out in support of the invention show that exemplary compounds 24, 26, and 27 produced no detectable breaks in protein-linked DNA, unlike VP-16.

From the foregoing, it can be seen how various objects of the invention are met. The invention provides 2-phenyl-4-quinolone compounds having significantly greater antitumor activity (nanomolar efficacy) than might reasonably have been expected from activities reported previously for 2-phenyl-4-quinolones. The compounds can be readily synthesized in good yield, and can be administered orally or parenterally to subjects in need of such treatment. Furthermore, the compounds show unexpectedly high antitumor activity for a broad range of cancer cell types, making them suitable for broad antitumor use.

The following examples are intended to illustrate but not in any way limit the scope of the invention.

EXAMPLES

Melting points were determined on a Fisher-John melting point apparatus and are uncorrected. Elemental analyses were performed by Atlantic Microlabs, Atlantic, Ga. $^1$H NMR spectra were measured at 300 MHz on a Bruker 300 spectrometer and recorded in $CDCl_3$, a mixture of $CDCl_3$ and $CD_3OD$, or DMSO-$d_6$. Chemical shifts are reported in δ (ppm) units relative to the internal reference $Me_4Si$. Infrared (IR) spectra were recorded on a Perkin Elmer IR 400 spectrometer as KBr pellets. Mass spectra (MS) data were obtained on a TRIO 1000 mass spectrometer. Flash chromatography was performed on silica gel (mesh 25–150 mm) using a mixture of $CHCl_3$ and MeOH as eluant.

Example 1: Syntheses

A. 3'-Amino-6,7-methylenedioxy-2-phenyl-4-quinolone (10). To a solution of 2-amino-4,5-methylenedioxyacetophenone (700 mg, 3.9 mmol) and $Et_3N$ (1.7 mL, 12.6 mmol) in THF (10 mL) at 0° C. was added dropwise 3'-nitrobenzoyl chloride (797 mg, 4.2 mol). After 30 min at 0° C., the mixture was stirred at r.t. for 2 h and poured into 20 mL ice water. The precipitate was collected and washed with water and MeOH. The solid (1.18 g, 92%) was dissolved in 200 mL of a mixture of EtOAc and MeOH (1:1) and hydrogenated over 10% Pd/C for 4 h. The catalyst was removed by filtration, and the solution was dried by evaporation. The solid residue was dried in vacuo, and suspended in 20 mL of t-BuOH. Potassium t-butoxide (1.55 g, 13.8 mmol) was added, and the mixture was heated at 70° C. under $N_2$ for 20 h. The mixture was cooled to room temperature (r.t.) and poured onto 30 mL of aqueous $NH_4Cl$ solution. The solid was collected and washed with distilled water (several times) and with a mixture of $CHCl_3$ and MeOH (1:10); amorphous; $^1$H NMR (DMSO-$d_6$) δ5.38 (br s, 2 H, $NH_2$), 6.11 (s, 1H, H-3), 6.14 (s, 2H, $OCH_2O$), 6.72 (dd, J=1.6, 7.5 Hz, 1H, H-4'), 6.86 (d, J=7.5 Hz, 1H, H-6'), 6.89 (d, J=1.6 Hz, 1H, H-2'), 7.18 (s, 1H, H-8), 7.19 (t, J=7.5 Hz, 1H, H-5'), 7.38 (s, 1H, H-5), 11.51 (br s, 1H, NH); IR (KBr) 3440, 3330, 3090, 1640 $cm^{-1}$; MS ($M^+$) 280.

B. 3'-N-Methylamino-6,7-methylenedioxy-2-phenyl-4-quinolone (11): obtained from 3'-N-methylaminoacetophenone and 2-amino-4,5-methylenedioxy-N,N-diethylbenzamide by the procedure reported previously (Li et al., 1994); amorphous; $^1$H NMR (DMSO-$d_6$) δ2.75 (d, J=4.5 Hz, 3H, NHCH$_3$), 5.96 (q, J=4.5 Hz, 1H, NHCH$_3$), 6.15 (s, 2H, OCH$_2$O), 6.17 (s, 1H, H-3), 6.71 (dd, J=1.8, 8.1 Hz, 1H, H-4'), 6.83 (d, J=1.8 Hz, 1H, H-2'), 6.89 (br d, J=8.1 Hz, 1H, H-6'), 7.20 (s 1H, H-8), 7.27 (t, J=8.1 Hz, 1H, H-5'), 7.39 (s, 1H, H-5), 11.51 (br s, 1H, NH); IR (KBr) 3340, 3240, 3090, 1630 (sh.) cm$^{-1}$; MS (M$^+$) 294.

C. 3'-Hydroxy-6,7-methylenedioxy-2-phenyl-4-quinolone (12): obtained from 3'-hydroxyacetophenone and 2-amino-4,5-methylenedioxy-N,N-diethylbenzamide by the procedure reported previously (Li et al., 1994); amorphous; $^1$H NMR (DMSO-$d_6$) δ6.15 (s, 2H, OCH$_2$O), 6.17 (s, 1H, H-3), 6.95 (dd, J=1.8, 8.0 Hz, 1H, H-4'), 7.12 (br s, 1H, H-2'), 7.18 (br d, J=8.0 Hz, 1H, H-6'), 7.20 (s, 1H, H-8), 7.37 (t, J=8.0 Hz, 1H, H-5'), 7.39 (s, 1H, H-5), 9.85 (s, 1 H, OH), 11.53 (br s, 1H, NH); IR (KBr) 3200, 3090, 1610 (sh) cm$^{-1}$; MS (M$^+$) 281.

D. 3'-Fluoro-6,7-methylenedioxy-2-phenyl-4-quinolone (13): obtained from 3'-fluorobenzoyl chloride and 2-amino-4,5-methylenedioxy-acetophenone (Li et al., 1994); amorphous; $^1$H NMR (DMSO-$d_6$) δ6.17 (s, 2H, OCH$_2$O), 6.33 (s, 1H, H-3), 7.19 (s, 1H, H-8), 7.40 (s, 1H, H-5), 7.41 (m, 1H, ArH of ring C), 7.65 (m, 3H, ArH3 of C ring); IR (KBr) 3440, 1635 cm$^{-1}$; MS (M$^+$) 283.

E. 3'-Chloro-6,7-methylenedioxy-2-phenyl-4-quinolone (14): obtained from 3'-chlorobenzoyl chloride and 2-amino-4,5-methylenedioxy-acetophenone (Li et al., 1994); amorphous; $^1$H NMR (DMSO-$d_6$) δ6.17 (s, 2H, OCH$_2$), 6.31 (s, 1H, H-3), 7.18 (s, 1H, H-8), 7.40 (s, 1H, H-5), 7.60 (t, J=8.0 Hz, 1H, H-5'), 7.64 (br dd, J=2.0, 8.0 Hz, 1H, H-6'), 7.77 (br dd, J=2.0, 8.0 Hz, 1H, H-4'), 7.89 (br s, 1H, H-2'), 11.63 (br s, 1H, NH); IR (KBr) 3090, 1640 cm$^{-1}$.

F. 3'-Bromo-6,7-methylenedioxy-2-phenyl-4-quinolone (15): obtained from 3'-bromobenzoyl chloride and 2-amino-4,5-methylenedioxy-acetophenone (Li et al., 1994); amorphous; $^1$H NMR (DMSO-$d_6$) δ6.17 (s, 2H, OCH$_2$O), 6.30 (s, 1H, H-3), 7.18 (s, 1H, H-8), 7.40 (s, 1H, H-5), 7.53 (t, J=8.0 Hz, 1H, H-5'), 7.76 (dd, J=2.0, 8.0 Hz, 1H, H-6'), 7.77 (dd, J=2.0, 8.0 Hz, 1H, H-4'), 8.01 (br s, 1H, H-2'); IR (KBr) 3080, 1620 cm$^{-1}$.

G. 3'-Trifluoromethyl-6,7-methylenedioxy-2-phenyl-4-quinolone (16): obtained from 3'-trifluoromethylbenzoyl chloride and 2-amino-4,5-methylenedioxyacetophenone (Li et al., 1994); amorphous; $^1$H NMR (DMSO-$d_6$) δ6.17 (s, 2H, OCH$_2$O), 6.35 (d, J=1.5 Hz, 1H, H-3), 7.18 (s, 1H, H-8), 7.41 (s, 1H, H-5), 7.81 (br t, J=7.9 Hz, 1H, H-5'), 7.94 (br d, J=7.9 Hz, 1H, H-6'), 8.11 (br d, J =7.9 Hz, 1H, H-4'), 8.14 (br s, 1H, H-2'), 11.71 (br s, 1H, NH); IR (KBr) 3090, 1620 cm$^{-1}$.

H. 3'-Trifluoromethoxy-6,7-methylenedioxy-2-phenyl-4-quinolone (17): obtained from 3'-trifluoromethoxybenzoyl chloride and 2-amino-4,5-methylenedioxyacetophenone (Li et al., 1994); amorphous; $^1$H NMR (DMSO-$d_6$) δ6.15 (s, 2H, OCH$_2$O), 6.61 (s, 1H, H-3), 7.17 (s, 1H, H-8), 7.44 (br d, J =8.0 Hz, 1H, H-4'), 7.53 (s, 1H, H-5), 7.61 (br s, 1H, H-2'), 7.63 (t, J=8.0 Hz, 1H, H-5'), 7.72 (br d, J=8.0 Hz, 1H, H-6'); IR (KBr) 3090, 1610 cm$^{-1}$.

I. 3'-Ethoxy-6,7-methylenedioxy-2-phenyl-4-quinolone (18): obtained from 3'-ethoxyacetophenone and 2-amino-4,5-methylenedioxy-N,N-diethylbenzamide by the procedure reported previously (Li et al., 1994); amorphous; $^1$H NMR (DMSO-$d_6$) δ1.37 (t, J=7.0 Hz, 3H, OCH$_2$CH$_3$), 4.14 (q, J=7.0 Hz, 2H, OCH$_2$CH$_3$), 6.16 (s, 2H, OCH$_2$O), 6.28 (s, 1H, H-3), 7.12 (br d, J=8.0 Hz, 1H, H-4'), 7.20 (s, 1H, H-8), 7.31 (br s, 1H, H-2'), 7.33 (t, J=8.0 Hz, 1H, H-6'), 7.39 (s, 1H, H-5), 7.47 (t, J=8.0 Hz, 1H, H-5'); IR (KBr) 3080, 1620 cm$^{-1}$; MS (M$^+$) 309.

J. 3'-Benzyloxy-6,7-methylenedioxy-2-phenyl-4-quinolone (19): obtained from 3'-benzyloxylacetophenone and 2-amino-4,5-methylenedioxy-N,N-diethylbenzamide by the procedure reported previously (Li et al., 1994); amorphous; $^1$H NMR (DMSO-$d_6$) δ5.22 (s, 2H, OCH$_2$Ph), 6.15 (s, 2H, OCH$_2$O), 6.29 (s, 1H, H-3), 7.20–7.50 (m, 10H, ArH); IR (KBr) 3090, 1620 cm$^{-1}$; MS (M$^+$) 371.

K. 3'-Chloro-6-amino-2-phenyl-4-quinolone (20): obtained from 3'-chlorobenzoyl chloride and 2-amino-5-nitroacetophenone (Simpson et al., 1945) as described as in the preparation of 10; amorphous; $_1$H NMR (DMSO-$d_6$) δ6.19 (s, 1H, H-3), 7.02 (dd, J=2.0, 8.5 Hz, 1H, H-4'), 7.20 (d, J=2.0 Hz, 1H, H-2'), 7.50 (br d, J=8.5 Hz, 1H, H-6'), 7.58 (t, J=8.5 Hz, 1H, H-5'), 7.59 (d, J=9.0 Hz, 1H, H-8), 7.75 (br d, J=9.0 Hz, 1H, H-7), 7.87 (br s, 1H, H-5), 11.49 (br s, 1H, NH); IR (KBr) 3340, 3360, 3080, 1630 cm$^{-1}$.

L. 3'-Trifluoromethyl-6-amino-2-phenyl-4-quinolone (21): obtained from 3'-trifluoromethylbenzoyl chloride and 2-amino-5-nitroacetophenone (Simpson et al., 1945) as described in the preparation of 10; amorphous; $^1$H NMR (DMSO-$d_6$) δ5.33 (br s, 2H, NH$_2$), 6.23 (s, 1H, H-3), 7.03 (dd, J=2.0, 8.8 Hz, 1H, H-7), 7.20 (d, J=2.0 Hz, 1H, H-5), 7.50 (d, J=8.8 Hz, 1H, H-8), 7.79 (br t, J=7.8 Hz, 1H, H-5'), 7.91 (br d, J=7.8 Hz, 1 H, H-6'), 8.09 (br d, J=7.8 Hz, 1H, H-4'), 8.12 (br s, 1H, H-2'), 11.56 (br s, 1H, NH); IR (KBr) 3390, 3280, 3090, 1620 cm$^{-1}$.

M. 3'-Methoxy-6-amino-2-phenyl-4-quinolone (22): obtained from 3'-methoxybenzoyl chloride and 2-amino-5-nitroacetophenone (Simpson et al., 1945) as described in the preparation of 10; amorphous; $^1$H NMR (DMSO-$d_6$) δ3.86 (s, 3H, OCH$_3$), 5.29 (br s, 1H, NH$_2$), 6.17 (s, 1H, H-3), 7.00 (dd, J=2.1, 8.7 Hz, 1H, H-7), 7.11 (br dd, J=1.7, 7.8 Hz, 1H, H-4'), 7.19 (d, J=2.1 Hz, 1H, H-5), 7.30 (br d, J=1.7 Hz, 1H, H-2'), 7.33 (br d, J=7.8 Hz, 1H, H-6'), 7.47 (t, J=7.8 Hz, 1H, H-5'), 7.51 (d, J=8.0 Hz, 1H, H-8), 11.40 (br s, 1H, NH); IR (KBr) 3340, 3240, 3090, 1600 cm$^{-1}$; MS (M$^+$) 266.

N. 3'-Methoxy-6-N,N-dimethylamino-2-phenyl-4-quinolone (23): obtained from 3'-methoxybenzoyl chloride and 2-amino-5-N,N-dimethylamino-acetophenone (Bandurco et al., 1987); amorphous; $^1$H NMR (DMSO-$d_6$) δ2.98 (s, 6H, N(CH$_3$)2), 3.87 (s, 3H, OCH$_3$), 6.27 (s, 1H, H-3), 7.12 (br dd, J=1.9, 7.9 Hz, 1H, H-4'), 7.23 (d, J=2.0, 1H, H-5), 7.30 (dd, J=2.0, 9.0 Hz, 1H, H-7), 7.34 (br d, J=1.9 Hz, 1H, H-2'), 7.37 (br dd, J=1.9, 7.9 Hz, 1H, H-6'), 7.49 (t, J=7.9 Hz, 1H, H-5'), 7.67 (d, J=9.0 Hz, 1H, H-8), 11.50 (br s, 1H, NH); IR (KBr) 3250, 3150, 3080, 1600 cm$^{-1}$; MS (M$^+$) 294.

O. 3'-Methoxy-6-chloro-2-phenyl-4-quinolone (24): obtained from 3'-methoxybenzoyl chloride and 2-amino-5-chloroacetophenone (Bandurco et al., 1987); amorphous; $^1$H NMR (DMSO-$d_6$) δ3.87 (s, 3H, OCH$_3$), 6.42 (s, 1H, H-3), 7.17 (br dd, J=1.9, 7.9 Hz, 1H, H-4'), 7.34 (br d, J=1.9 Hz, 1H, H-2'), 7.39 (br d, J=7.9 Hz, 1H, H-6'), 7.51 (t, J=7.9 Hz, 1H, H-5'), 7.72 (dd, J=1.9, 8.9 Hz, 1H, H-7), 7.81 (d, J=8.9 Hz, 1H, H-8), 8.03 (d, J=1.9 Hz, 1H, H-5); IR (KBr) 3090, 1630 cm$^{-1}$.

P. 3'-Fluoro-6-acetamido-2-phenyl-4-quinolone (25): obtained from 3'-fluorobenzoyl chloride and 2-amino-5-acetamidoacetophenone (Simpson et al., 1945); amorphous; $^1$H NMR (DMSO-$d_6$) δ2.08 (s, 3H, COCH$_3$), 6.34 (s, 1H, H-3), 7.43 (dt, J=2.0, 7.0 Hz, 1H, H-5'), 7.59–7.73 (m, 5H, H-5, 8, 2', 4', 6'), 7.89 (dd, J=2.5, 9.0 Hz, 1H, H-7); IR (KBr) 3300, 3180, 3100, 1660, 1640 cm$^{-1}$.

Q. 3'-Chloro-6-acetamido-2-phenyl-4-quinolone (26): obtained from 3-chlorobenzoyl chloride and 2-amino-5- acetamidoacetophenone (Simpson et al., 1945); amorphous; $^1$H NMR (DMSO-d$_6$) δ2.08 (s, 3H, COCH$_3$), 6.32 (d, J=1.4 Hz, 1H, H-3), 7.60 (br t, J=7.8 Hz, 1H, H-5), 7.64 (br dd, J=1.9, 7.8 Hz, 1H, H-6'), 7.70 (d, J=8.9 Hz, 1H, H-8), 7.79 (br dd, J=1.9, 7.8 Hz, 1H, H-4'), 7.90 (dd, J=2.2, 8.9 Hz, 1H, H-7), 7.92 (br s, 1H, H-2'), 8.32 (d, J=2.2 Hz, 1H, H-5), 10.15 (br s, I H, NH), 11.75 (br s, 1H, NH); IR (KBr) 3300, 3180, 3100, 1660, 1630 cm$^{-1}$; MS (M$^+$) 270.

R. 3'-Methoxy-6-acetamido-2-phenyl-4-quinolone (27): obtained from 3'-methoxybenzoyl chloride and 2-amino-5-acetamidoacetophenone (Simpson et al., 1945); amorphous; $^1$H NMR (DMSO-d$_6$) δ2.08 (s, 3H, COCH$_3$), 3.87 (s, 3H, OCH$_3$), 6.30 (s, 1H, H-3), 7.14 (dd, J=1.5, 8.5 Hz, 1H, H-4'), 7.35 (br s, 1H, H-2'), 7.38 (br d, J=8.5 Hz, 1H, H-6'), 7.50 (t, J=8.5 Hz, 1H, H-5'), 7.71 (d, J=9.0 Hz, 1H, H-8), 7.88 (dd, J=1.5, 9.0 Hz, 1H, H-7), 8.32 (d, J=1.5 Hz, 1H, H-5); IR (KBr) 3280, 3170, 3090, 1680, 1640 cm$^{-1}$.

S. 3'-Methoxy-6-pyrrolinyl-2-phenyl-4-quinolone (28): obtained from 3'-methoxybenzoyl chloride and 2-amino-5-pyrrolinylacetophenone (Bandurco et al., 1987); amorphous; $^1$H NMR (DMSO-d$_6$) δ2.00 (m, 4H, CH$_2$CH$_2$NCH$_2$CH$_2$), 2.50 (m, 4H, CH$_2$NCH$_2$), 6.26 (s, 1H, H-3), 7.03 (br s, 1H, H-5), 7.11 (dd, J=1.5, 8.5 Hz, 2H, H-4', H-7), 7.34 (br s, 1H, H-2'), 7.37 (br d, J=8.5 Hz, 1H, H-6'), 7.48 (t, J=8.5 Hz, 1H, H-5'), 7.67 (d, J=9.1 Hz, 1H, H-8), 11.48 (br s, 1H, NH); IR (KBr) 3240, 3090, 1600 cm$^{-1}$.

T. 3'-Trifluoromethoxy-6-pyrrolinyl-2-phenyl-4-quinolone (29): obtained from 3'-trifluoromethoxybenzoyl chloride and 2-amino-5-pyrrolidinylacetophenone (Bandurco et al., 1987); amorphous; $^1$H NMR (DMSO-d$_6$) δ2.09 (m, 4H, CH$_2$CH$_2$NCH$_2$CH$_2$), 3.41 (m, 4H, CH$_2$NCH$_2$), 6.56 (s, 1H, H-3), 7.13 (dd, J=2.7, 9.0 Hz, 1H, H-7), 7.22 (d, J=2.7 Hz, 1H, H-5), 7.39 (br d, J=7.9 Hz, 1H, H-4'), 7.60 (t, J=7.9 Hz, 1H, H-5'), 7.63 (br d, J=1.9 Hz, 1H, H-2'), 7.65 (d, J=9.0 Hz, 1H, H-8), 7.72 (br d, J=7.9 Hz, 1H, H-6'); IR (KBr) 3260, 3100, 1600 cm$^{-1}$.

U. 3'-Methoxy-6-piperidinyl-2-phenyl-4-quinolone (30): obtained from 3'-methoxybenzoyl chloride and 2 amino-5-piperidinylacetophene (Bandurco et al., 1987); amorphous; MS (M$^+$) 334.

V. 3'-Methoxy-6-morpholinyl-2-phenyl-4-quinolone (31): obtained from 3'-methoxybenzoyl chloride and 2-amino-5-morpholinylacetophenone (Bandurco et al., 1987); amorphous; $^1$H NMR (DMSO-d$_6$) δ3.16 (t, J=4.7 Hz, 4H, CH$_2$NCH$_2$), 3.78 (t, J=4.7 Hz, 4H, CH$_2$OCH$_2$), 3.87 (s, 3H, OCH$_3$), 6.30 (d, J=1.5 Hz, 1H, H-3), 7.13 (dd, J=3.0, 8.0 Hz, 1H, H-4'), 7.34 (d, J=3.0 Hz, 1H, H-2'), 7.36 (br d, J=8.0 Hz, 1H, H-6'), 7.44 (d, J=2.5 Hz, 1H, H-5), 7.49 (t, J=9.0 Hz, 1H, H-5'), 7.50 (dd, J=2.5, 9.0 Hz, 1H, H-7), 7.69 (d, J=9.0 1H, H-8); IR (KBr) 3250, 3090, 1600 cm$^{-1}$; MS (M$^+$) 349.

W. 3'-Methoxy-6-methylpiperazinyl-2-phenyl-4-quinolone (32): obtained from 3-methoxybenzoyl chloride and 2-amino-5-methylpiperazinyl-acetophenone (Bandurco et al., 1987); amorphous; $^1$H NMR (DMSO-d$_6$) δ2.25 (s, 3H, N-CH$_3$), 3.18, 3.31 (both m, 4 H each, (NCH$_2$CH$_2$N) ×2), 3.87 (s, 3H, OCH$_3$), 6.29 (d, J=1.5 Hz, 1H, H-3), 7.13 (dd, J=2.0, 8.0 Hz, 1H, H-4'), 7.34 (dd, J=2.0, 2.0 Hz, 1H, H-2'), 7.37 (br d, J =8.0 Hz, 1H, H-6'), 7.42 (d, J=2.5 Hz, 1H, H-5), 7.48 (dd, J=2.5, 9.0 Hz, 1H, H-7), 7.49 (t, J=8.0 Hz, 1H, H-5'), 7.67 (d, J=9.0 Hz, 1H, H-8); IR (KBr) 3280, 3160, 3090, 1670, 1650 cm$^{-1}$; MS (M$^+$) 349.

X. 3'-Methoxy-6'-benzamido-2-phenyl-4-quinolone (33): obtained from 3'-methoxybenzoyl chloride and 2-amino-5-benzamidoacetophenone. 2-Amino-5-benzamidoacetophenone was prepared from 2-nitro-5-aminoacetophenone (Simpson et al., 1945) and 3-methoxybenzoyl chloride; amorphous.

Example 2

Biochemical Assays

Electrophoretically homogeneous bovine brain tubulin was purified as described previously (Hamel, et al., 1984). Combretastatin A-4 was a generous gift of Dr. G. R. Pettit, Arizona State University. Dihydrocombretastatin A-4 was prepared as described previously (Getahun et al., 1992). [3H]Colchicine was obtained from Dupont, nonradiolabeled colchicine from Sigma, podophyllotoxin from Aldrich, and monosodium glutamate from USB. The binding of radiolabeled colchicine to tubulin was measured by the DEAE-cellulose filter technique, as described previously (Kuo, et al., 1993). Reaction mixtures contained 1.0 mM tubulin, 5.0 mM [3H]colchicine, and 5.0 mM potential inhibitor.

The tubulin polymerization assay was performed as described previously (Li et al., 1994). In brief, tubulin at 1.2 mg/mL (12 mM) was preincubated for 15 min at 26° C. in a 0.24 mL volume in 0.8M monosodium glutamate (pH 6.6 with NaOH in a 2M stock solution) with varying drug concentrations. The drug stock solutions were in dimethyl sulfoxide, and the final solvent concentration was 4% (v/v). Atomic absorption spectroscopy indicated the Mg$^{2+}$ concentration of the reaction mixtures was about 35 mM (26–27 mM from the glutamate, 8–9 mM from the tubulin), but no exogenous magnesium was added. All concentrations are in terms of the final reaction volume (0.25 mL). The reaction mixtures were chilled on ice, and 10 mL of 10 mM GTP was added to each reaction mixture. Samples were transferred to cuvettes held at 0° C. by an electronic temperature controller in Gilford spectrophotometers. Baselines were established at 350 nm, and polymerization initiated by a temperature jump to 26° C. The jump took about 50 sec to complete. After 20 min, turbidity readings were recorded, and the temperature controller was set to 0° C. When depolymerization was complete, turbidity readings were again recorded. Generally, turbidity readings were about 90% cold-reversible, and the cold-reversible turbidity was taken to represent the extent of assembly for each reaction mixture. IC$_{50}$ values were obtained graphically from inhibition of polymerization by different drug concentrations. Four spectrophotometers were used for each experimental sequence, with at least two control reactions (no drug) in each set. Generally, the control reactions were within 5% of their average. A minimum of three independent IC$_{50}$ values was obtained for each drug, except that inactive compounds were usually evaluated only two times. In most cases, IC$_{50}$ values obtained with this polymerization assay are highly reproducible. Generally, standard deviations were within 20% of the mean values, but in some cases the standard deviations were 30–35% from the mean. Therefore, we can conservatively estimate that a 50% difference in IC$_{50}$ values represents a difference in the relative activity of two agents.

Although the invention has been described with respect to particular embodiments, it will be appreciated that various changes and modifications can be made without departing from the invention.

It is claimed:

1. A method of inhibiting tumor cell growth in a mammalian subject, comprising administering to the subject a therapeutically effective amount of a 2-phenyl-4-quinolone compound represented by the formula:

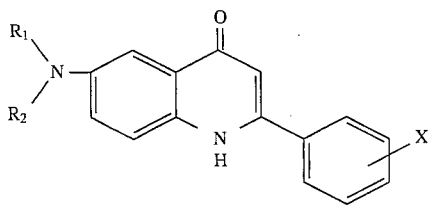

wherein X is a selected from the group consisting of H, F, Cl, Br, I, CH$_3$, CF$_3$, OH, OCH$_3$, OCF$_3$, OCH$_2$CH$_3$, NH$_2$, NHCH$_3$, N(CH$_3$)$_2$, O-benzyl, —C(=O)—R$_0$, —C(=O)—OR$_0$, where R$_0$ is a lower alkyl group; and where R$_1$ and R$_2$ (i) are lower alkyl groups or (ii) taken together, form a chain having the form —(CH$_2$)$_m$Y(CH$_2$)$_n$—, where Y is CH$_2$, O, or S; m and n are each greater than 1; and the sum of m and n is between 3 and 6.

2. The method of claim 1, wherein X is a meta substituent.

3. The method of claim 2, wherein X is OCH$_3$ or OCF$_3$.

4. The method of claim 3, wherein NR$_1$R$_2$ is selected from the group consisting of N(CH$_3$)$_2$, N-pyrrolidinyl, N-piperidyl, and N-morpholinyl.

5. The method of claim 4, wherein X is OCH$_3$.

6. The method of claim 5, wherein NR$_1$R$_2$ is N(CH$_3$)$_2$, N-pyrrolidinyl, or N-morpholinyl.

7. The method of claim 6, wherein NR$_1$R$_2$ is N-pyrrolidinyl.

8. The method of claim 3, wherein X is OCF$_3$.

9. The method of claim 8, wherein NR$_1$R$_2$ is N(CH$_3$)$_2$, N-pyrrolidinyl, or N-morpholinyl.

10. The method of claim 9, wherein NR$_1$R$_2$ is N-pyrrolidinyl.

11. A 2-phenyl-4-quinolone compound represented by the formula

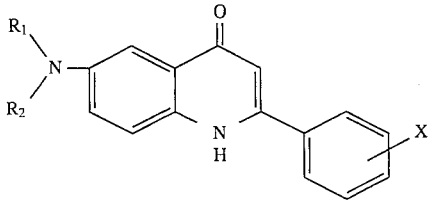

wherein X is a selected from the group consisting of H, F, Cl, Br, I, CH$_3$, CF$_3$, OH, OCH$_3$, OCF$_3$, OCH$_2$CH$_3$, NH$_2$, NHCH$_3$, N(CH$_3$)$_2$, O-benzyl, —C(=O)—R$_0$, —C(=O)—OR$_0$, where R$_0$ is a lower alkyl group; and where R$_1$ and R$_2$ (i) are lower alkyl groups or (ii) taken together, form a chain having the form —(CH$_2$)$_m$Y(CH$_2$)$_n$—, where Y is CH$_2$, O, or S; m and n are each greater than 1; and the sum of m and n is between 3 and 6.

12. The compound of claim 11, wherein X is a meta substituent.

13. The compound of claim 12, wherein X is OCH$_3$ or OCF$_3$.

14. The compound of claim 13, wherein NR$_1$R$_2$ is selected from the group consisting of N(CH$_3$)$_2$, N-pyrrolidinyl, N-piperidyl, and N-morpholinyl.

15. The compound of claim 14, wherein X is OCH$_3$.

16. The compound of claim 15, wherein NR$_1$R$_2$ is N(CH$_3$)$_2$, N-pyrrolidinyl, or N-morpholinyl.

17. The compound of claim 16, wherein NR$_1$R$_2$ is N-pyrrolidinyl.

18. The compound of claim 13, wherein X is OCF$_3$.

19. The compound of claim 18, wherein NR$_1$R$_2$ is N(CH$_3$)$_2$, N-pyrrolidinyl, or N-morpholinyl.

20. The compound of claim 19, wherein NR$_1$R$_2$ is N-pyrrolidinyl.

* * * * *